(12) United States Patent
Yagyu

(10) Patent No.: US 11,776,803 B2
(45) Date of Patent: Oct. 3, 2023

(54) UV IRRADIATION APPARATUS

(71) Applicant: Ushio Denki Kabushiki Kaisha, Tokyo (JP)

(72) Inventor: Hideaki Yagyu, Tokyo (JP)

(73) Assignee: Ushio Denki Kabushiki Kaisha, Tokyo (JP)

(*) Notice: Subject to any disclaimer, the term of this patent is extended or adjusted under 35 U.S.C. 154(b) by 169 days.

(21) Appl. No.: 17/399,647

(22) Filed: Aug. 11, 2021

(65) Prior Publication Data
US 2022/0059336 A1 Feb. 24, 2022

(30) Foreign Application Priority Data
Aug. 21, 2020 (JP) ................. 2020-140018

(51) Int. Cl.
*H01J 61/16* (2006.01)
*H01J 61/06* (2006.01)
*H01J 65/04* (2006.01)
*A61L 2/10* (2006.01)

(52) U.S. Cl.
CPC .............. *H01J 61/16* (2013.01); *H01J 61/06* (2013.01); *H01J 65/046* (2013.01); *A61L 2/10* (2013.01)

(58) Field of Classification Search
CPC .......... H01J 65/00; H01J 65/046; H01J 61/16; H01J 61/04; H01J 61/06; H01J 61/54; H01J 61/125; A61L 2/10
See application file for complete search history.

(56) References Cited

U.S. PATENT DOCUMENTS

| 5,049,777 A | 9/1991 | Mechtersheimer |
| 2005/0046331 A1 | 3/2005 | Kim et al. |
| 2021/0335593 A1 | 10/2021 | Taniguchi et al. |

FOREIGN PATENT DOCUMENTS

| JP | 2013-171660 A | | 9/2013 |
| JP | 2013171660 A | * | 9/2013 |
| JP | 2017-068944 A | | 4/2017 |
| JP | 2018-055965 A | | 4/2018 |
| JP | 2018055965 A | * | 4/2018 |
| JP | 2020-092968 A | | 6/2020 |

(Continued)

OTHER PUBLICATIONS

International Search Report and Written Opinion of the International Searching Authority issued in PCT/JP2021/022286; dated Jul. 20, 2021.

(Continued)

*Primary Examiner* — David E Smith
*Assistant Examiner* — Hsien C Tsai
(74) *Attorney, Agent, or Firm* — Studebaker & Brackett PC

(57) ABSTRACT

To improve startability in a UV irradiation apparatus equipped with excimer lamps. The UV irradiation apparatus includes a plurality of excimer lamps each having a light-emitting tube filled with a discharge gas containing a noble gas. The plurality of excimer lamps includes a first excimer lamp filled with the discharge gas at a first enclosed gas pressure and a second excimer lamp filled with the discharge gas at a second enclosed gas pressure lower than the first enclosed gas pressure. The first excimer lamp is placed in a position such that at least part of light emitted from the second excimer lamp is allowed to enter the first excimer lamp.

20 Claims, 6 Drawing Sheets

(56) References Cited

FOREIGN PATENT DOCUMENTS

WO      2019/080981 A2    5/2019
WO      WO-2020121934 A1 *   6/2020   ............... A61L 2/10

OTHER PUBLICATIONS

The partial European search report (R. 64 EPC) issued by the European Patent Office dated Jan. 21, 2022, which corresponds to European Patent Application No. 21190067.5-1212 and is related to U.S. Appl. No. 17/399,647.
Communication pursuant to Article 94(3) EPC issued by the European Patent Office dated May 13, 2022, which corresponds to European Patent Application No. 21190067.5-1212 and is related to U.S. Appl. No. 17/399,647.

* cited by examiner

UV IRRADIATION APPARATUS

BACKGROUND OF THE INVENTION

Field of the Invention

The present invention relates to a UV irradiation apparatus and particularly relates to a UV irradiation apparatus equipped with excimer lamps.

Description of the Related Art

A lamp utilizing dielectric-barrier discharge hereinafter referred to as an "excimer lamp") is conventionally known which is allowed to emit light by applying a voltage to a discharge gas enclosed within its light-emitting tube through a dielectric material such as quartz glass.

Such an excimer lamp has a specific emission wavelength depending on the type of discharge gas or the combination of discharge gases. For example, excimer lamps are known which use, as a discharge gas, a noble gas such as argon (Ar), krypton (Kr), or xenon (Xe) or a mixed gas of the noble gas and a halogen gas such as fluorine (F), chlorine (Cl), iodine (I), or bromine (Br). For example, Patent Document 1 listed below states that various lights whose peak wavelengths belong to the range of 126 nm to 308 nm can be obtained by changing the type of discharge gas or the combination of discharge gases.

PRIOR ART DOCUMENT

Patent Document

Patent Document 1: JP 2017-068944 A

SUMMARY OF THE INVENTION

Demands for UV irradiation apparatuses equipped with excimer lamps have recently been growing, and such UV irradiation apparatuses have come to be used in a wider variety of situations. The UV irradiation apparatuses are mainly intended to be used in industry in which they are expected to always be turned on for a long period, but from now on, it is also expected that there will be many situations where they are turned on and off repeatedly during use.

However, some excimer lamps have poor startability, and some of them are difficult to turn on after a long turn-off period.

In light of the above problem, it is an object of the present invention to improve the startability of a UV irradiation apparatus equipped with excimer lamps.

The present invention is directed to a UV irradiation apparatus including:
- a plurality of excimer lamps each having a light-emitting tube filled with a discharge gas containing a noble gas, wherein the plurality of excimer lamps include
- a first excimer lamp filled with the discharge gas at a first enclosed gas pressure, and
- a second excimer lamp filled with the discharge gas at a second enclosed gas pressure lower than the first enclosed gas pressure, and
- the first excimer lamp is placed in a position such that at least part of light emitted from the second excimer lamp is allowed to enter the first excimer lamp.

Increasing the enclosed gas pressure of the discharge gas sealed inside the excimer lamp's light-emitting tube will extend the life of the excimer lamp. The reason for this will be explained with an example of a case where the discharge gas is KrCl.

When voltage is applied to the light-emitting tube filled with the discharge gas, discharge occurs in the light-emitting tube (in a discharge space) so that krypton gas (Kr) and chlorine gas ($Cl_2$) present in the light-emitting tube are excited or ionized by electrons emitted by discharge to generate KrCl* (krypton-chloride exciplex), The KrCl* is a very unstable compound, and is therefore separated into Kr and $Cl_2$ in a short time, and at this time, specific light (excimer light) is emitted. The excimer lamp filled with such type of discharge gas emits ultraviolet light having a peak wavelength of about 222 nm.

In such a case as described above, part of the discharge gas (especially, Cl) with energy having been increased by repeated discharge is struck into the tube wall (bulb) of the light-emitting tube, and as a result, the number of atoms constituting the discharge gas reduces with time. This reduces the amount of KrCl* generated, resulting in a gradual decrease in irradiance. Although there is a difference in the tendency of the speed at which the irradiance decreases, this problem is inherent in excimer lamps regardless of the type of discharge gas.

As described above, in these latter days when demands for UV irradiation apparatuses equipped with excimer lamps have been growing, it is important to extend the lives of UV irradiation apparatuses by increasing their irradiance maintenance rate after long-time use. In light of this situation, it is considered effective to increase the number of atoms that are the gas species of the discharge gas in advance, or in other words, to increase the enclosed gas pressure, as a way to increase the irradiance maintenance rate.

However, an increase in the enclosed gas pressure of the discharge gas sealed inside the light-emitting tube causes another problem of a reduction in startability. This is based on Paschen's law. As described above, in these latter days when UV irradiation apparatuses equipped with excimer lamps have come to be used in a wider variety of situations, an improvement in startability is important, and therefore there is a background that the sacrifice of startability to increase irradiance maintenance rate needs to be avoided as much as possible.

Startability may be improved by increasing voltage. However, an increase in input voltage may cause a power supply system or a cooling system to become larger, which may limit the use of the UV irradiation apparatuses.

The above-described UV irradiation apparatus is equipped with a plurality of excimer lamps (a first excimer lamp and a second excimer lamp) different in enclosed gas pressure. As mentioned above, startability improves as the enclosed gas pressure reduces. Therefore, the second excimer lamp with lower enclosed gas pressure can achieve higher startability than the first excimer lamp with higher enclosed gas pressure. That is, when the UV irradiation apparatus is operated, the second excimer lamp out of the plurality of excimer lamps housed in a casing tends to be turned on first.

In the above-described structure, the first excimer lamp is placed in a position such that at least part of light emitted from the second excimer lamp is allowed to enter the first excimer lamp. Therefore, light emitted from the second excimer lamp that is turned on first enters the first excimer lamp. As a result, the startability of the first excimer lamp is improved by the light emitted from the second excimer lamp as a trigger.

That is, according to the above-described UV irradiation apparatus, the first excimer lamp with higher enclosed gas pressure can be started in a time almost equivalent to the starting time of the second excimer lamp with lower enclosed gas pressure. In addition, since the UV irradiation apparatus is equipped with the first excimer lamp with higher enclosed gas pressure, a higher irradiance maintenance rate is achieved compared to the case where only the second excimer lamp is installed.

Further, the UV irradiation apparatus is only required to have a structure such that voltage can be applied to the extent that at least the second excimer lamp with lower enclosed gas pressure can be turned on, and therefore does not need to have a large power supply system. That is, the UV irradiation apparatus can achieve both high startability and high irradiance maintenance rate while its power supply system and cooling system are downsized.

Furthermore, by using the same type of discharge gas sealed in the first excimer lamp and the second excimer lamp, when both are turned on, the same emission spectrum can be achieved as when only the first excimer lamp or the second excimer lamp is installed.

As described above, the degree of a reduction in the startability of an excimer lamp caused by increasing the enclosed gas pressure of a discharge gas depends on the type of discharge gas. Particularly, the problem of a reduction in startability becomes remarkable when the excimer lamp uses a mixed gas of a noble gas and a halogen gas as a discharge gas. That is when a UV irradiation apparatus equipped with such a plurality of excimer lamps using, as a discharge gas, a mixed gas of a noble gas, and a halogen gas employs the above-described structure, the effect described above can remarkably be obtained.

Particularly, the problem of startability is remarkable for an excimer lamp using, as a discharge gas, a mixed gas of $Kr$ and $Cl_2$. Therefore, when a UV irradiation apparatus equipped with a plurality of excimer lamps using, as a discharge gas, such a mixed gas employs the above-described structure, the effect described above can particularly remarkably be obtained.

An excimer lamp using, as a discharge gas, a mixed gas of $Kr$ and $Cl_2$ emits ultraviolet light having a peak wavelength of about 222 nm. Even when the skin of a human body is exposed to ultraviolet light in a wavelength band of 190 nm or more and 230 nm or less including 222 nm, the ultraviolet light is absorbed by the stratum corneum of the skin and does not reach layers deeper than the stratum corneum (stratum basale side). Corneocytes contained in the stratum corneum are dead cells, and therefore, unlike the case of irradiation with ultraviolet light having a wavelength of, for example, 254 nm, there is substantially no risk that the ultraviolet light is absorbed by living cells in the stratum spinosum, the stratum granulosum, and the dermis so that DNA is destroyed.

It is known that ultraviolet light in the above-described wavelength band has the effect of killing germs on an object irradiated therewith. Therefore, an UV irradiation apparatus equipped with excimer lamps filled with the above-described discharge gas is expected to be used in various applications such as photosterilization and is considered to be used in a wide variety of situations.

The above-described structure makes it possible for a UV irradiation apparatus having a photosterilization effect to achieve both an improvement in startability and an increase in irradiance maintenance rate and to downsize its power supply system. Particularly, a UV irradiation apparatus having a photosterilization effect is expected to be used also for the sterilization of a small space, and therefore it can be said that a UV irradiation apparatus having the above-described structure which can achieve both high startability and high irradiance maintenance rate while having a compact size is very highly effective for use in photosterilization.

A pressure difference between the second enclosed gas pressure and the first enclosed gas pressure may be set to 5% or more of the second enclosed gas pressure.

Such a structure is expected to have the effect of significantly reducing the start-up time of the first excimer lamp (e.g., 1 second or more).

The above-described UV irradiation apparatus may include an LED element, in which the LED element is placed so that light emitted from the LED element is allowed to enter at least the second excimer lamp.

The enclosed gas pressure of the discharge gas sealed in the second excimer lamp is low, but it can be considered that there is a case where it takes time for the second excimer lamp to start up only by itself. However, the above-described structure makes it possible to reduce the start-up time of the second excimer lamp because the second excimer lamp can receive light emitted from the LED element provided as a start-up auxiliary light source. It is to be noted that, as described above, when the second excimer lamp is turned on, the first excimer lamp is turned on at almost the same time by receiving light emitted from the second excimer lamp.

If the UV irradiation apparatus includes only the first excimer lamp having higher enclosed gas pressure without the second excimer lamp having lower enclosed gas pressure, high startability cannot be achieved even when the LED element is provided as a start-up auxiliary light source. This is because the light emitted from the second excimer lamp has extremely higher energy than the light emitted from the LED element, and is therefore highly effective at starting up the first excimer lamp.

The plurality of excimer lamps may include two or more of the first excimer lamps.

Even when the UV irradiation apparatus is equipped with the plurality of first excimer lamps, light emitted from the second excimer lamp enters each of the first excimer lamps, and therefore startability improves. This structure makes it possible to achieve a long-life UV irradiation apparatus having high startability and high irradiance because a plurality of first excimer lamps having a high irradiance maintenance rate is provided.

In the above-described structure, the plurality of excimer lamps may include the second excimer lamps whose number is smaller than that of the first excimer lamps.

In this case, the plurality of excimer lamps may include two or more of the second excimer lamps.

Such a structure makes it possible to, even if one of the second excimer lamps cannot be turned on due to problems, turn on the first excimer lamps by the other second excimer lamp(s).

The first excimer lamp and the second excimer lamp may be placed in a direction not parallel to tube axes of respective light-emitting tubes in a same plane, and
  the above-described UV irradiation apparatus may further
    include a pair of electrode blocks placed so as to be in contact with a portion of each of the light-emitting tubes of the first excimer lamp and the second excimer lamp and to be separated from each other in a direction parallel to the tube axes.

Such a structure makes it possible to reduce the scale of the apparatus because electrodes for applying a voltage to each of the excimer lamps can be made common.

It is to be noted that the above-described UV irradiation apparatus may include a casing that accommodates the plurality of excimer lamps. In this case, the first excimer lamp in the casing is placed in a position such that at least part of light emitted from the second excimer lamp is allowed to enter the first excimer lamp.

According to the present invention, it is possible to improve the startability of a UV irradiation apparatus equipped with excimer lamps.

DETAILED DESCRIPTION OF THE PREFERRED EMBODIMENTS

An embodiment of a UV irradiation apparatus according to the present invention will be described regarding the drawings. It is to be noted that all the following drawings are schematically shown, and the dimensional ratios of the drawings are not necessarily consistent with actual dimensional ratios. Further, the dimensional ratios of the drawings are not necessarily consistent with each other.

Figure 1:
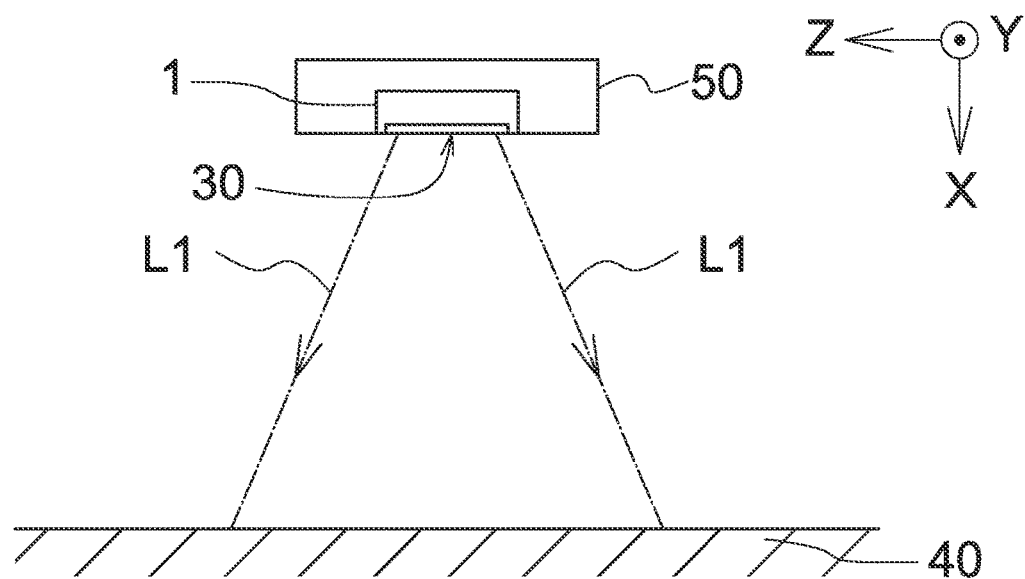
FIG. 1 is a diagram schematically showing one mode of use of a UV irradiation apparatus according to the present invention.

FIG. 1 is a diagram schematically showing one mode of use of the UV irradiation apparatus according to the present invention. FIG. 1 schematically shows how an area 40 to be irradiated is irradiated with ultraviolet light L1 emitted through a light extraction face 30 of a UV irradiation apparatus 1 installed in a housing 50.

Figure 2:
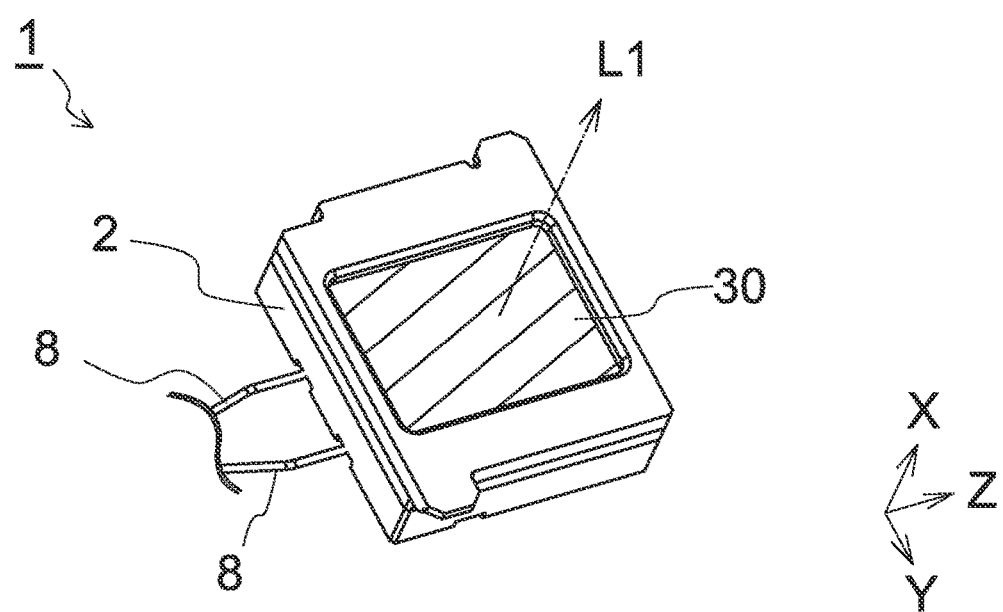
FIG. 2 is a perspective view schematically showing an example of the appearance of the UV irradiation apparatus.
Figure 3:
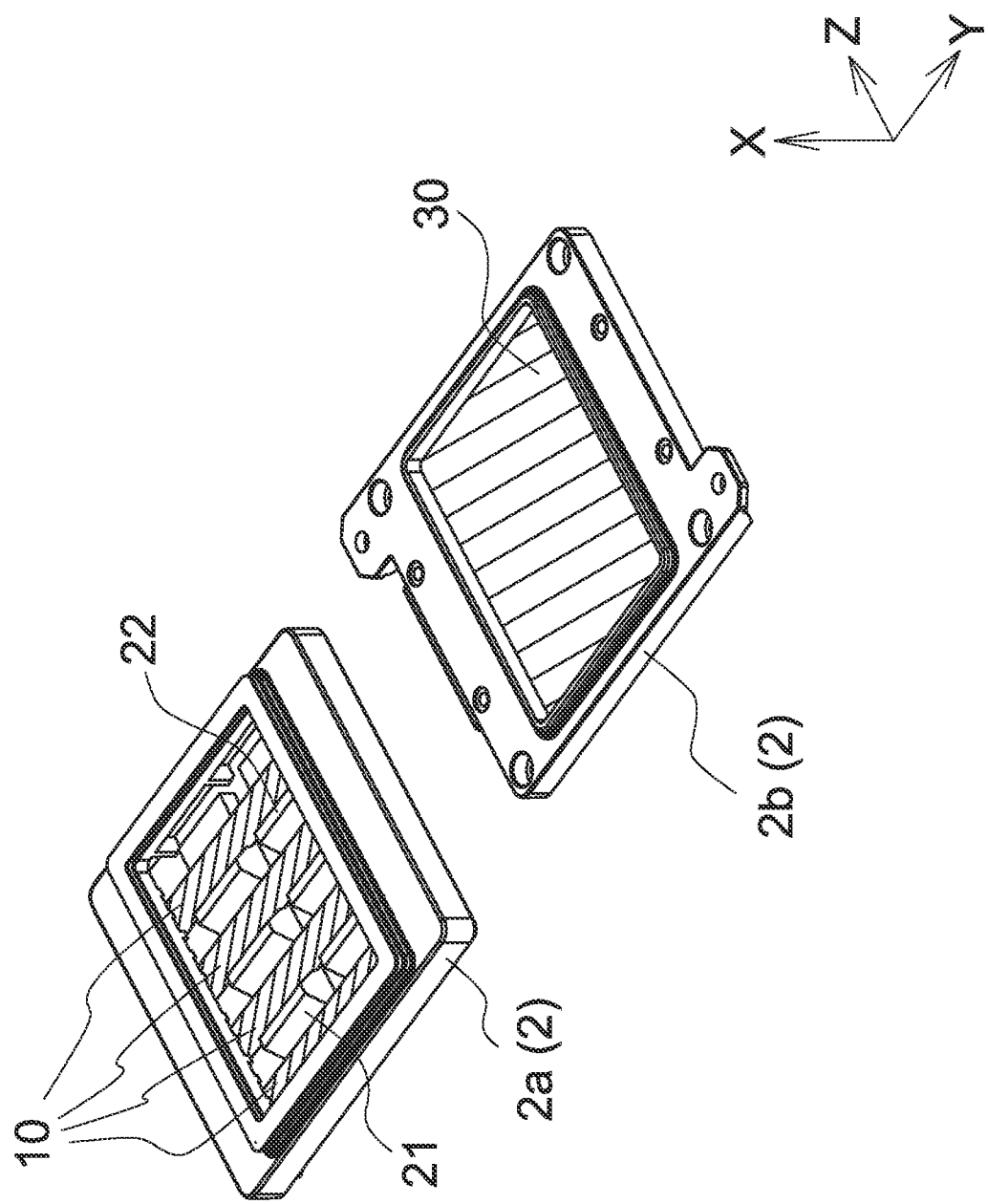
FIG. 3 is an exploded perspective view of FIG. 2, in which a casing is separated into a main body and a lid.

FIG. 2 is a perspective view schematically showing an example of the appearance of the UV irradiation apparatus 1. FIG. 3 is an exploded perspective view of FIG. 2, in which a casing 2 of the UV irradiation apparatus 1 is separated into a main body 2a and a lid 2b.

The following description regarding the drawings will be made using an X-Y-Z coordinate system in which a direction in which ultraviolet light L1 is extracted is defined as an X direction and a plane orthogonal to the X direction is defined as a YZ plane. More specifically, as will be described later regarding FIGS. 2 to 7 and FIG. 9, the direction of tube axis of an excimer lamp 10 is defined as a Y direction, and a direction orthogonal to the X and Y directions is defined as a Z direction.

In the following description, when a distinction is made between a positive direction and a negative direction to express a direction, a positive or negative sign is given like "+X direction" or "−X direction". When a direction is expressed without making a distinction between a positive direction and a negative direction, the term "direction" is simply used like "X direction", That is, the term. "X direction" used herein includes both a "−X direction" and a "−X direction". The same goes for the Y direction and the Z direction.

As shown in FIG. 2 and FIG. 3, the UV irradiation apparatus 1 includes a casing 2 having a light extraction face 30 formed in one of the surfaces thereof. The casing 2 includes a main body 2a and a lid 2b, and the main body 2a houses a plurality of excimer lamps 10 and electrode blocks (21, 22) therein. In this embodiment, four excimer lamps 10 are housed in the casing 2 by way of example.

Figure 4:
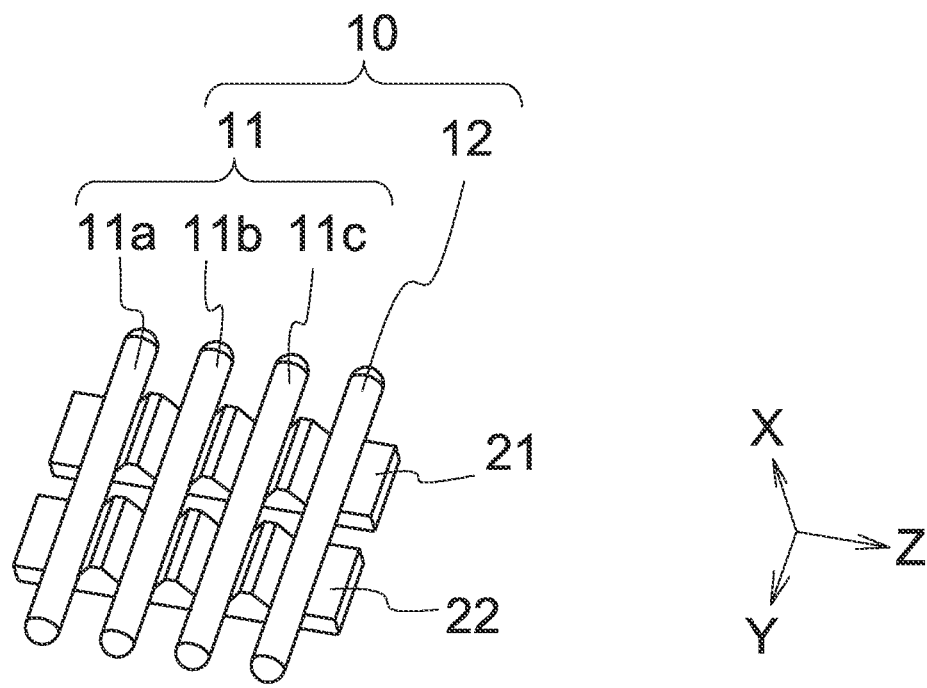
FIG. 4 is a schematic perspective view of a plurality of excimer lamps and electrode blocks extracted from FIG. 3.
Figure 5:
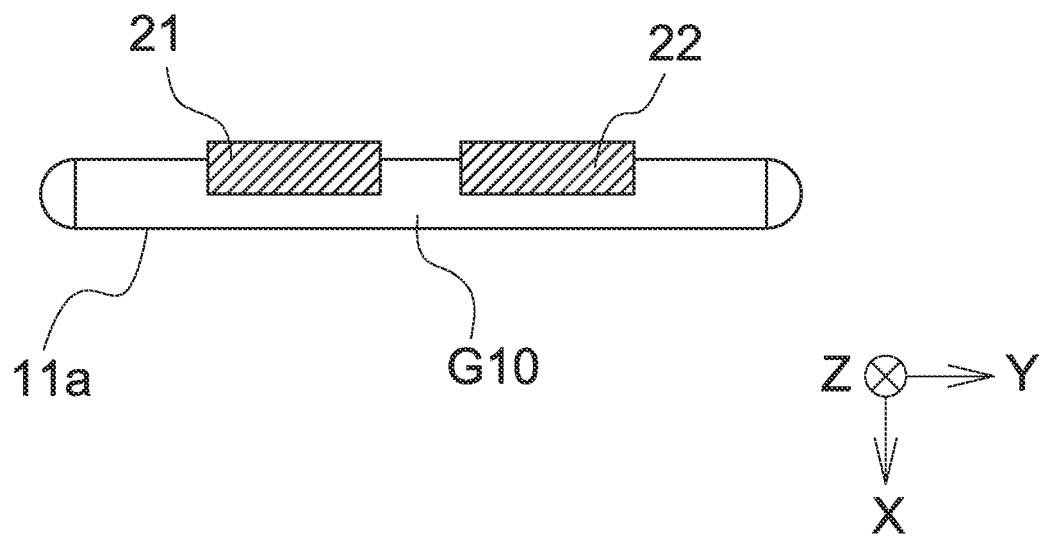
FIG. 5 is a schematic plan view for explaining a positional relationship between the excimer lamps and the electrode blocks, which is obtained by viewing the excimer lamps in a +Z direction.

FIG. 4 is a schematic perspective view of the plurality of excimer lamps 10 and the electrode blocks (21, 22) extracted from FIG. 3. FIG. 5 is a schematic view showing a positional relationship between the excimer lamps 10 and the electrode blocks (21, 22), which corresponds to a schematic plan view obtained by viewing the excimer lamps 10 in the +Z direction.

As shown in FIG. 4, the UV irradiation apparatus 1 according to this embodiment includes four excimer lamps 10 placed so as to be separated from each other in the Z direction. Further, two electrode blocks (21, 22) are placed so as to be in contact with a portion of the outer surface of the light-emitting tube of each of the excimer lamps 10.

The plurality of excimer lamps 10 includes a first excimer lamp 11 and a second excimer lamp 12. The gas species of a discharge gas G10 sealed inside the light-emitting tube of the first excimer lamp 11 and that sealed inside the light-emitting tube of the second excimer lamp 12 are the same, but the first excimer lamp 11 and the second excimer lamp 12 are different in enclosed gas pressure. The first excimer lamp 11 is filled with the discharge gas G10 at a first enclosed gas pressure P1. On the other hand, the second excimer lamp 12 is filled with the discharge gas G10 at a second enclosed gas pressure P2 lower than the first enclosed gas pressure P1.

FIG. 4 shows a case where the plurality of excimer lamps 10 includes three first excimer lamps 11 (11a, 11b, 11c) and one second excimer lamp 12. Hereinbelow, both the first excimer lamp 11 and the second excimer lamp 12 are collectively called "excimer lamps 10".

Each of the excimer lamps 10 has a light-emitting tube whose tube axis is parallel to the Y direction, and the outer surface of the light-emitting tube of each of the excimer lamps 10 is in contact with the electrode blocks (21, 22) in positions separated from each other in the Y direction. That is, both the electrode blocks (21, 22) are placed to straddle across each of the excimer lamps 10 in the Z direction while being in contact with the outer surface of the light-emitting tube of each of the excimer lamps 10.

As described above, the UV irradiation apparatus 1 according to this embodiment includes a pair of electrode blocks (21, 22), and they are placed in positions separated from each other in the Y direction. The electrode blocks (21, 22) are made of an electrically conductive material, preferably a material having the property of reflecting ultraviolet light emitted from the excimer lamps 10. For example, the electrode blocks (21, 22) are made of Al, an Al alloy, or stainless steel.

When a high-frequency AC voltage of, for example, about 1 kHz to 5 MHz is applied between the electrode blocks (21, 22), the voltage is applied to the discharge gas G10 sealed inside the light-emitting tube of each of the excimer lamps 10 through the light-emitting tube. The gas species of the discharge gas G10 is not particularly limited as long as atoms constituting the gas species are excited or ionized into an excimer state by the application of such voltage and then excimer light is emitted when the atoms are returned to a ground state. More specifically, the discharge gas G10 may be one or more of noble gases such as argon (Ar), krypton (Kr), and xenon (Xe) or a mixed gas of the noble gas and a halogen gas such as fluorine (F), chlorine (Cl), iodine (I), or bromine (Br).

For example, the discharge gas G10 may be a mixed gas of krypton (Kr), chlorine (Cl), and argon (Ar). It is to be noted that in this case, krypton and chlorine function as a light-emitting gas, and argon functions as a buffer gas. As a buffer gas, at least one noble gas selected from argon (Ar), neon (Ne), and helium (He) can be used.

Figure 6:
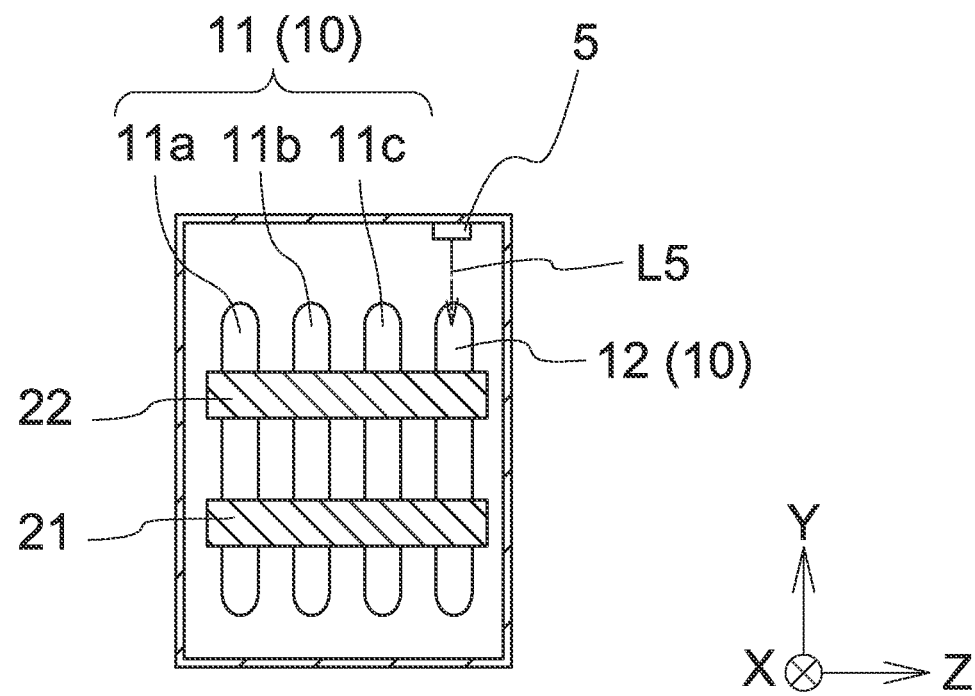
FIG. 6 is a plan view schematically showing the excimer lamps and the electrode blocks viewed on the opposite side from a light extraction face.

FIG. 6 is a plan view schematically showing the excimer lamps 10 and the electrode blocks (21, 22) placed in the main body 2a of the casing 2, which is viewed on the opposite side from the light extraction face 30 (in the +X direction). The UV irradiation apparatus 1 according to this embodiment includes an LED element 5. The LED element 5 is provided as a start-up auxiliary light source to aid the start-up of the second excimer lamp 12 in particular.

The LED element 5 is, for example, a light source that emits light L5 having a peak wavelength of 250 nm or more and 300 nm or less. However, when the UV irradiation apparatus 1 includes the LED element 5, the wavelength of the light L5 emitted from the LED element 5 is not limited as long as the light L5 has the function of aiding the start-up of the second excimer lamp 12. The wavelength of the light L5 emitted from the LED element 5 is appropriately selected within the range of 200 nm or more and 0.500 nm or less including an ultraviolet light range and a blue light range.

When the UV irradiation apparatus 1 is operated, a high-frequency voltage is applied between the electrode blocks (21, 22) as described above through power wires 8 (see FIG. 2) from a power source not shown. This allows the high-frequency voltage to be applied to the discharge gas G10 sealed inside each of the excimer lamps 10 through the light-emitting tube.

However, there is a case where the discharge gas G10 sealed inside the excimer lamps 10 does not emit excimer light by the application of high-frequency voltage alone. Particularly, the first excimer lamps 11 filled with the discharge gas G10 at a high first enclosed gas pressure P1 are not turned on or require a very long time to be turned on by the application of voltage alone.

In the UV irradiation apparatus 1 according to this embodiment, a voltage is applied between the electrode blocks (21, 22), and an electrical current is supplied from a power source not shown to the LED element 5. This makes it possible to turn on the LED element 5 and irradiate the second excimer lamp 12 with the light L5 emitted from the LED element 5.

When the light L5 emitted from the LED element 5 enters the second excimer lamp 12 in a state where a voltage is applied to the discharge gas G10 through the electrode blocks (21, 22), the second excimer lamp 12 is turned on in a short time within 0.1 seconds to 5 seconds) by the optical energy of the light L5 as a trigger.

There is a case where the light L5 emitted from the LED element 5 enters also the first excimer lamps 11. However, the first excimer lamps 11 are filled with the discharge gas G10 at a higher enclosed gas pressure than the second excimer lamp 12, and therefore it is difficult to turn on the first excimer lamps 11 quickly by optical energy derived from the light L5 emitted from the LED element 5. That is, the first excimer lamps 11 are not usually turned on before the second excimer lamp 12 is turned on.

Figure 7:
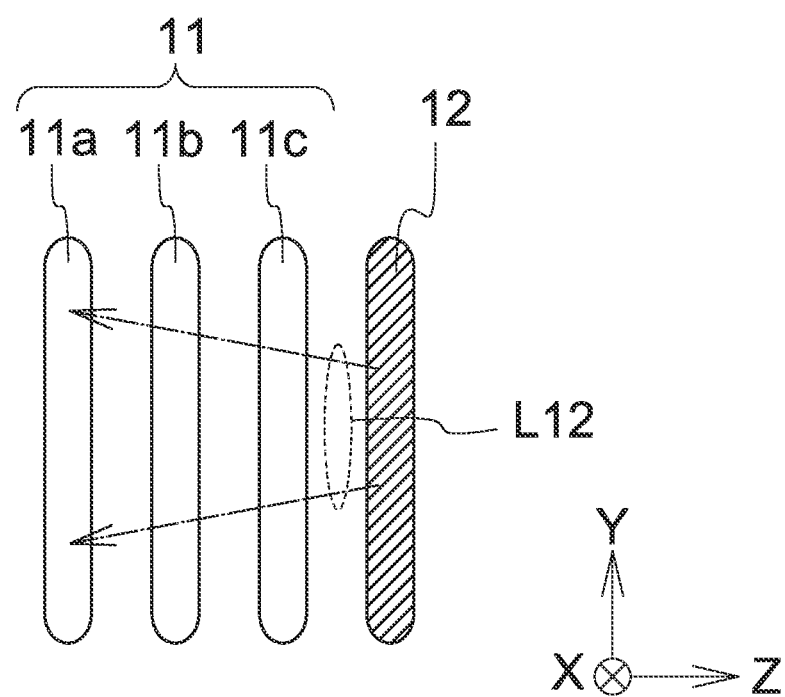
FIG. 7 is a diagram schematically showing how ultraviolet light emitted from a second excimer lamp enters first excimer lamps.

As shown in FIG. 7, when the second excimer lamp 12 is turned on, excimer light (ultraviolet light L12) having a wavelength derived from the discharge gas G10 is emitted from the second excimer lamp 12. This ultraviolet light L12 travels toward the outer circumference of the light-emitting tube, and therefore the first excimer lamps 11 placed in the Z direction are also irradiated with the ultraviolet light L12. The ultraviolet light L12 has much higher optical energy than the light L5 emitted from the LED element 5. Therefore, when the ultraviolet light L12 emitted from the second excimer lamp 12 enters the first excimer lamps 11 in a state where voltage is applied to the discharge gas G10 through the electrode blocks (21, 22), the first excimer lamps 11 are turned on almost at the same time by the optical energy of the ultraviolet light L12 as a trigger.

Figure 8:
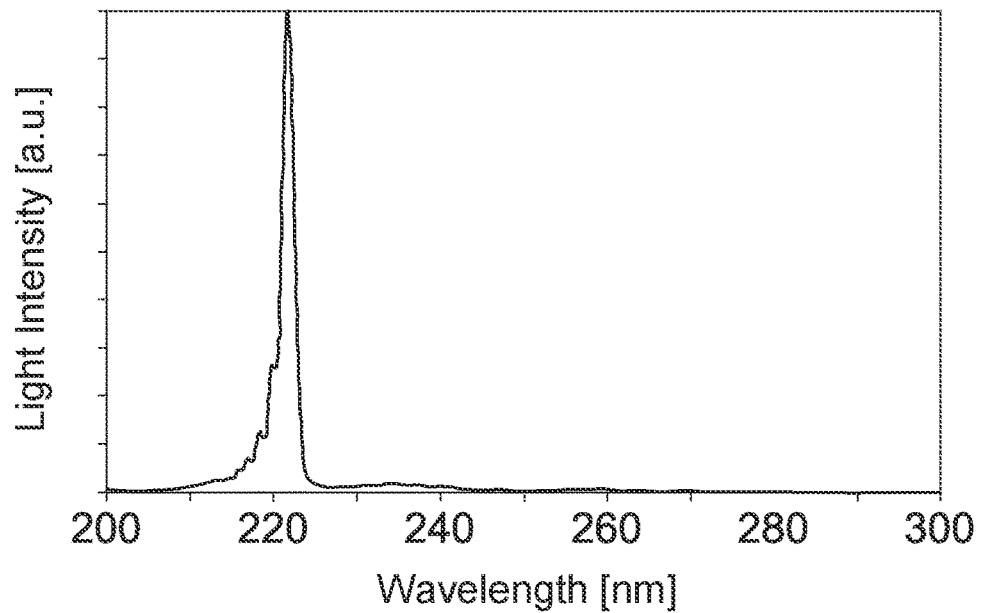
FIG. 8 shows an example of a spectrum waveform of ultraviolet light emitted from an excimer lamp filled with a discharge gas containing Kr and Cl.

The first excimer lamps 11 are filled with the discharge gas G10 whose gas species is the same as the discharge gas G10 sealed inside the second excimer lamp 12. Therefore, ultraviolet light L11 emitted from the lighted first excimer lamps 11 is emitted as ultraviolet light L1 having the same spectrum toward the area 40 to be irradiated through the light extraction face 30 together with the ultraviolet light L12 emitted from the second excimer lamp 12. When the discharge gas G10 contains krypton (Kr) and chlorine (Cl), the ultraviolet light L1 emitted from the UV irradiation apparatus 1 has such a spectrum as shown in FIG. 8.

From the viewpoint of increasing irradiance maintenance rate, the enclosed gas pressure of the discharge gas G10 sealed inside the excimer lamps 10 is preferably high. However, increasing the enclosed gas pressure of the discharge gas G10 causes the time required for the excimer lamps 10 to be turned on after the application of voltage (start-up time) to become longer. This point will be explained with reference to Table 1 shown below.

Table 1 shows the result of verification of a relationship between the enclosed gas pressure of the discharge gas G10 and the start-up time. The method of the verification will be described.

TABLE 1

| Sample No. | Enclosed gas pressure (kPa) | Enclosed gas pressure Deviation | Start-up DelayTime (see) |
|---|---|---|---|
| #1 | 20 | 0.0% | 0 |
| #2 | 20.5 | 2.5% | 0 |
| #3 | 21 | 5.0% | 1 |
| #4 | 22 | 10.0% | 2 |
| #5 | 25 | 25.0% | 10 |

A sample having the same structure as the above-described LV irradiation apparatus 1 was prepared, and all the four excimer lamps 10 were filled with the discharge gas G10 at the same enclosed gas pressure. As the discharge gas G10, a mixed gas obtained by mixing krypton, chlorine, and neon in a ratio of Kr:Cl$_2$:Ne=40:1:59 was used.

It is to be noted that each Sample #1 to #5 mutually differed in the enclosed gas pressure of the discharge gas G10 (see Table 1).

A voltage of 4 kV was applied to each Sample #1 to #5 from a power source not shown in the figure, and the time from the start of voltage application to the start of lighting-up was measured. It is to be noted that the time was measured by placing a light-receiving sensor on the light extraction face 30 of each. Sample #1 to #5 and measuring a time lag between the time when voltage application was started and the time when the light was detected by the light-receiving sensor.

As can be seen from Table 1 that Samples #3 to #5, in which the enclosed gas pressure of the discharge gas G10 sealed inside the excimer lamps 10 is relatively high, have a slower start-up time than Sample #1, in which the enclosed gas pressure is relatively low. Further, as a result of comparison among Samples #3 to #5, it is also confirmed that the start-up time becomes longer as the enclosed gas pressure of the discharge gas G10 increases.

It is to be noted that as shown in Table 1, there could not be confirmed a difference of 1 second or more in start-up time between Sample #1 and Sample #2. This is because the system used for verification could not detect a time lag of less than 1 second, but in reality, it is estimated that start-up is delayed by about 0.1 seconds to 0.5 seconds.

However, it is considered that, in a situation in which the UV irradiation apparatus 1 is practically used, start-up delay does not matter too much in many cases as long as the start-up delay time is less than 1 second. On the other hand, a start-up delay time of 1 second or more may cause a problem for users. Furthermore, when the startup delay time reaches 10 seconds, as in sample #5, a significant problem can arise in situations where the excimer lamp 10 is repeatedly turned on and off, as it takes time to turn on the excimer lamp 10 each time the operation of the UV irradiation apparatus 1 is started.

On the other hand, as described above, an increase in the enclosed gas pressure of the discharge gas G10 sealed inside the excimer lamps 10 is preferred from the viewpoint of increasing the irradiance maintenance rate of the excimer lamps 10 for life extension, That is, it can be said that a uniform reduction in the enclosed gas pressure of the discharge gas G10 enclosed within the excimer lamps TO is not preferred from the viewpoint of irradiance maintenance rate.

As described above, the UV irradiation apparatus 1 according to this embodiment includes a second excimer lamp 12 with lower enclosed gas pressure and a first excimer lamp 11 with higher enclosed gas pressure, and the first excimer lamp 11 is placed in a position such that ultraviolet light L12 emitted from the second excimer lamp 12 is allowed to enter the first excimer lamp 11. Therefore, when the second excimer lamp 12 that quickly starts up is turned on, the first excimer lamp 11 can be turned on at almost the same time as the second excimer lamp 12 by the ultraviolet light L12 emitted from the second excimer lamp 12 as a trigger.

The UV irradiation apparatus 1 is equipped with a first excimer lamp 11 with higher enclosed gas pressure, which improves the irradiance maintenance rate compared to the case where only a second excimer lamp 12 with lower enclosed gas pressure is equipped.

The second excimer lamp 12 has a lower irradiance maintenance rate than the first excimer lamp 11 due to the lower enclosed gas pressure of the discharge gas G10. Therefore, long-term use reduces irradiance derived from the ultraviolet light L12 emitted from the second excimer lamp 12, However, since the rate of decrease in irradiance derived from the ultraviolet light Lit emitted from the first excimer lamp 11 is slow, the rate of decrease in irradiance is suppressed as for the ultraviolet light L1 irradiated from the light extraction face 30 of the UV irradiation apparatus 1.

Particularly, in light of the results in Table 1, it can be seen that by setting the second enclosed gas pressure P2 so that the pressure difference from the first enclosed gas pressure P1 is 5% or more of the second enclosed gas pressure P2, and by equipping the UV irradiation apparatus 1 with the second excimer lamp 12 in which the discharge gas G10 is enclosed at this second enclosed gas pressure P2, the start-up time of the UV irradiation apparatus 1 can be shortened by 1 second or more.

Further, it is also confirmed from the result shown in Table 1 that the effect of shortening the start-up time gradually becomes remarkable as the pressure difference between the second enclosed gas pressure P2 and the first enclosed gas pressure P1 increases. Therefore, the pressure difference between the second enclosed gas pressure P2 and the first enclosed gas pressure P1 may be set to 10% or more of the second enclosed gas pressure P2, or even 25% or more.

It is to be noted that from the viewpoint that the start-up time is shortened while the reduction speed of irradiance maintenance rate of the ultraviolet light L1 emitted from the UV irradiation apparatus 1 is slowed down as much as possible, the number of the first excimer lamps 11 is preferably larger than that of the second excimer lamps 12.

Other Embodiments

Hereinbelow, other embodiments will be described.

Figure 9A:
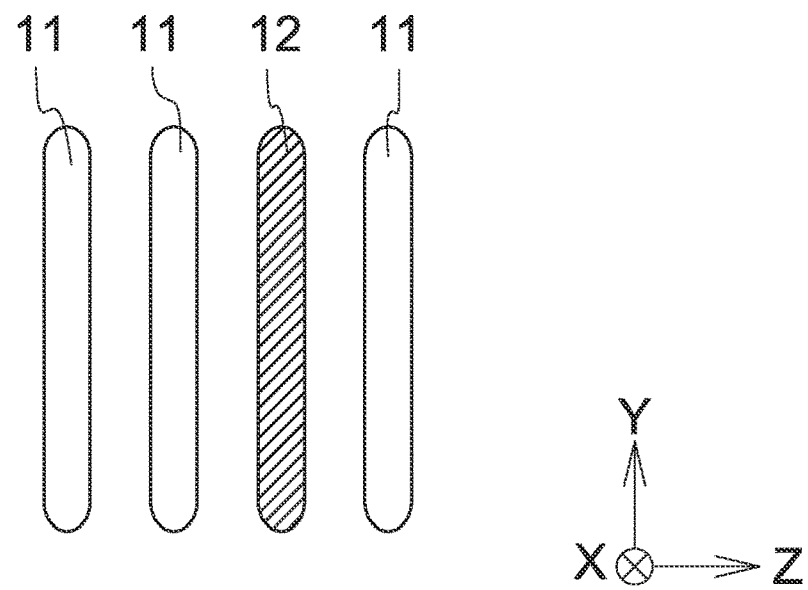
FIG. 9A is a diagram showing another example of the pattern of placement of the first and second excimer lamps.
Figure 9B:
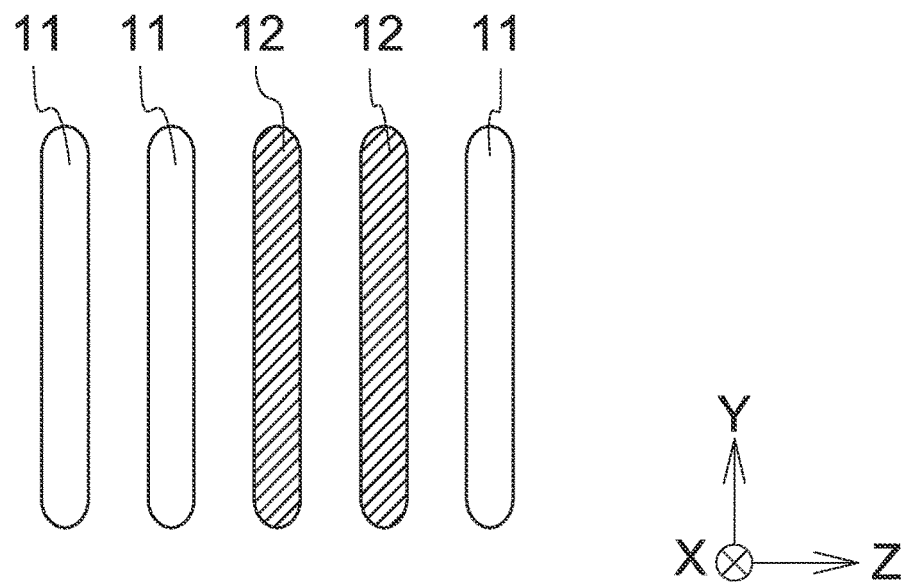
FIG. 9B is a diagram showing another example of the pattern of placement of the first and second excimer lamps.

<1> The above embodiment has been described in a case where the second excimer lamp 12 is located outermost among the plurality of excimer lamps 10 placed in the Z direction. However, the second excimer lamp 12 may be located in any position. For example, as shown in FIG. 9A, the second excimer lamp 12 may be located near the center with the first excimer lamps 11 on both sides of it.

<2> The UV irradiation apparatus 1 may include two or more second excimer lamps 12. For example, the UV irradiation apparatus 1 schematically shown in FIG. 9B includes three first excimer lamps 11 and two second excimer lamps 12. In the present invention, the number of the first excimer lamps 11 and the number of the second excimer lamps 12 in the UV irradiation apparatus 1 are not limited.

Figure 9C:
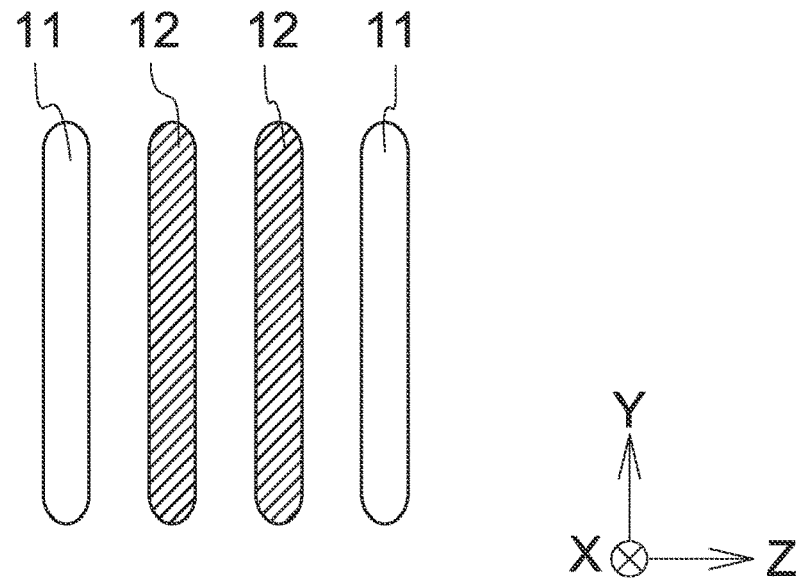
FIG. 9C is a diagram showing another example of the pattern of placement of the first and second excimer lamps.

For example, as shown in FIG. 9C, the UV irradiation apparatus 1 may include two first excimer lamps 11 and two second excimer lamps 12. Alternatively, the UV irradiation apparatus 1 may include one first excimer lamp 11 and one second excimer lamp 12.

<3> When the UV irradiation apparatus 1 includes two or more first excimer lamps 11, these first excimer lamps 11 may be different from each other in the enclosed gas pressure of the discharge gas G10. Similarly, when the UV irradiation apparatus 1 includes two or more second excimer lamps 12, these second excimer lamps 12 may be different from each other in the enclosed gas pressure of the discharge gas (110. In other words, the UV irradiation apparatus 1 including three or more excimer lamps 10 different from each other in enclosed gas pressure is also within the scope of the present invention as long as the UV irradiation apparatus 1 includes a first excimer lamp 11 having a relatively high enclosed gas pressure of the discharge gas (110 and a second excimer lamp 12 having a relatively low enclosed gas pressure of the discharge gas G10.

<4> The above embodiment has been described with reference to a case where the UV irradiation apparatus 1 includes an LED element 5 for start-up aid. However, in the present invention, the UV irradiation apparatus 1 may or may not include the LED element 5. The UV irradiation apparatus 1 does not necessarily need to include the LED element 5 when the startability of the second excimer lamp 12 is originally high or when start-up of the second excimer lamp 12 is aided by a means other than the LED element 5, such as a trigger electrode.

<5> The above embodiment has been described with reference to a case where the excimer lamps 10 included in the UV irradiation apparatus 1 are placed in the Z direction orthogonal to the direction of the tube axes of the light-emitting tubes (Y direction), However, such placement of the plurality of excimer lamps 10 is merely an example. For example, the plurality of excimer lamps 10 may be placed in a direction not parallel to the Y direction, other than the Z direction. Alternatively, some of the plurality of excimer lamps 10 may be placed in a state where they are shifted in the X direction.

<6> The shape of the excimer lamps 10 included in the UV irradiation apparatus 1 and the shape and placement of the electrode blocks (21, 22) for applying voltage to each of the excimer lamps 10 are not particularly limited, and the present invention is not limited to those described above with reference to FIG. 2 to FIG. 6.

<7> The casing 2 that houses the excimer lamps 10 does not necessarily need to have a closed space. For example, the casing 2 may have a shape such that its one side is open and the other three sides are closed.

Further, the UV irradiation apparatus 1 does not necessarily need to include the casing 2. In other words, the present invention includes a case where the excimer lamps 10 installed in the UV irradiation apparatus 1 are completely exposed.

What is claimed is:

1. A UV irradiation apparatus comprising:
 a plurality of excimer lamps each having a light-emitting tube filled with a discharge gas containing a noble gas, wherein the plurality of excimer lamps includes
 a first excimer lamp filled with the discharge gas at a first enclosed gas pressure, and
 a second excimer lamp filled with the discharge gas at a second enclosed gas pressure lower than the first enclosed gas pressure;
 the first excimer lamp is placed in a position such that at least part of light emitted from the second excimer lamp is allowed to enter the first excimer lamp;
 the first excimer lamp and the second excimer lamp are arranged in a direction orthogonal to the light-emitting tube axis of the respective excimer lamps;
 the UV irradiation apparatus further comprises a pair of electrode blocks placed so as to be in contact with a portion of each of the light-emitting tubes of the first excimer lamp and the second excimer lamp and to be separated from each other in a direction parallel to the tube axes; and
 when voltage is applied between the pair of electrode blocks, the first and second excimer lamps are turned on almost simultaneously.

2. The UV irradiation apparatus according to claim 1, wherein a pressure difference between the second enclosed gas pressure and the first enclosed gas pressure is set to 5% or more of the second enclosed gas pressure.

3. The UV irradiation apparatus according to claim 1, further comprising an LED element,
 wherein the LED element is placed so that light emitted from the LED element is allowed to enter at least the second excimer lamp.

4. The UV irradiation apparatus according to claim 1, wherein the plurality of excimer lamps include two or more of the first excimer lamps.

5. The UV irradiation apparatus according to claim 4, wherein the plurality of excimer lamps include the second excimer lamps whose number is smaller than that of the first excimer lamps.

6. The UV irradiation apparatus according to claim 5, wherein the plurality of excimer lamps include two or more of the second excimer lamps.

7. The UV irradiation apparatus according to claim 1, wherein the discharge gas contains a halogen gas in addition to the noble gas.

8. The UV irradiation apparatus according to claim 7, wherein the discharge gas is a mixed gas of Kr and $Cl_2$.

9. The UV irradiation apparatus according to claim 1, wherein
 the first excimer lamp and the second excimer lamp are placed in a same plane.

10. The UV irradiation apparatus according to claim 2, further comprising an LED element,
 wherein the LED element is placed so that light emitted from the LED element is allowed to enter at least the second excimer lamp.

11. The UV irradiation apparatus according to claim 2, wherein the plurality of excimer lamps include two or more of the first excimer lamps.

12. The UV irradiation apparatus according to claim 3, wherein the plurality of excimer lamps include two or more of the first excimer lamps.

13. The UV irradiation apparatus according to claim 10, wherein the plurality of excimer lamps include two or more of the first excimer lamps.

14. The UV irradiation apparatus according to claim 2, wherein
 the first excimer lamp and the second excimer lamp are placed in a direction not parallel to tube axes of respective light-emitting tubes in a same plane; and
 the UV irradiation apparatus further comprises a pair of electrode blocks placed so as to be in contact with a portion of each of the light-emitting tubes of the first excimer lamp and the second excimer lamp and to be separated from each other in a direction parallel to the tube axes.

15. The UV irradiation apparatus according to claim 3, wherein
 the first excimer lamp and the second excimer lamp are placed in a direction not parallel to tube axes of respective light-emitting tubes in a same plane; and
 the UV irradiation apparatus further comprises a pair of electrode blocks placed so as to be in contact with a portion of each of the light-emitting tubes of the first excimer lamp and the second excimer lamp and to be separated from each other in a direction parallel to the tube axes.

16. The UV irradiation apparatus according to claim 4, wherein
 the first excimer lamp and the second excimer lamp are placed in a direction not parallel to tube axes of respective light-emitting tubes in a same plane; and
 the UV irradiation apparatus further comprises a pair of electrode blocks placed so as to be in contact with a portion of each of the light-emitting tubes of the first excimer lamp and the second excimer lamp and to be separated from each other in a direction parallel to the tube axes.

17. The UV irradiation apparatus according to claim 5, wherein
the first excimer lamp and the second excimer lamp are placed in a direction not parallel to tube axes of respective light-emitting tubes in a same plane; and
the UV irradiation apparatus further comprises a pair of electrode blocks placed so as to be in contact with a portion of each of the light-emitting tubes of the first excimer lamp and the second excimer lamp and to be separated from each other in a direction parallel to the tube axes.

18. The UV irradiation apparatus according to claim 6, wherein
the first excimer lamp and the second excimer lamp are placed in a direction not parallel to tube axes of respective light-emitting tubes in a same plane; and
the UV irradiation apparatus further comprises a pair of electrode blocks placed so as to be in contact with a portion of each of the light-emitting tubes of the first excimer lamp and the second excimer lamp and to be separated from each other in a direction parallel to the tube axes.

19. The UV irradiation apparatus according to claim 7, wherein
the first excimer lamp and the second excimer lamp are placed in a direction not parallel to tube axes of respective light-emitting tubes in a same plane; and
the UV irradiation apparatus further comprises a pair of electrode blocks placed so as to be in contact with a portion of each of the light-emitting tubes of the first excimer lamp and the second excimer lamp and to be separated from each other in a direction parallel to the tube axes.

20. The UV irradiation apparatus according to claim 8, wherein
the first excimer lamp and the second excimer lamp are placed in a direction not parallel to tube axes of respective light-emitting tubes in a same plane; and
the UV irradiation apparatus further comprises a pair of electrode blocks placed so as to be in contact with a portion of each of the light-emitting tubes of the first excimer lamp and the second excimer lamp and to be separated from each other in a direction parallel to the tube axes.

\* \* \* \* \*